US00PP34789P2

(12) United States Plant Patent
Meilland

(10) Patent No.: US PP34,789 P2
(45) Date of Patent: Dec. 6, 2022

(54) HYBRID TEA ROSE PLANT NAMED 'MEICATESS'

(50) Latin Name: *Rosa hybrida*
Varietal Denomination: MEICATESS

(71) Applicant: The Conard Pyle Company, West Grove, PA (US)

(72) Inventor: Alain Antoine Meilland, Antibes (FR)

(73) Assignee: The Conard Pyle Company, West Grove, PA (US)

( * ) Notice: Subject to any disclaimer, the term of this patent is extended or adjusted under 35 U.S.C. 154(b) by 0 days.

(21) Appl. No.: 17/738,121

(22) Filed: May 6, 2022

(30) Foreign Application Priority Data

Jul. 6, 2021 (QZ) ..... PBR 2021/1798

(51) Int. Cl.
*A01H 5/02* (2018.01)
*A01H 6/74* (2018.01)

(52) U.S. Cl.
USPC ..... Plt./130

(58) Field of Classification Search
USPC ..... Plt./130, 138, 139, 107, 108, 102
CPC ... A01H 5/02; A01H 5/00; A01H 6/74; A01H 6/749
See application file for complete search history.

(56) References Cited

PUBLICATIONS

Jardinerie Animalerie Fleuriste translate 2021, retrieved Jun. 15, 2022 at https://www-jardinerie--animalerie-fleuriste-fr.translate.goog/actualites/les-fines-fleurs-createurs-de-roses-roseraies-meilland-une-reference-absolue-pour-les-jardiniers-et-les-fleuristes/658626/?_x . . . ,6 pp. (Year: 2021).*

Pharmarosa Romantic Roses—Sapling Rose, retrieved on Aug. 9, 2022 at https://pharmarosahigh-it.translate.goog/rozsa/ruban-rouge-723?_x_tr_sl=it&_x_tr_tl=en&_x_tr_hl=en&_x_tr_pto=sc, 7 pp. (Year: 2022).*

* cited by examiner

*Primary Examiner* — June Hwu
(74) *Attorney, Agent, or Firm* — Panitch Schwarze Belisario & Nadel LLP; Stephany G. Small; Travis W. Bliss

(57) ABSTRACT

A new and distinct variety of rose plant, referred to by its cultivar name, 'MEICATESS', is disclosed. The new variety forms attractive, very double dark pink colored flowers. Attractive glossy foliage is formed, which contrasts beautifully with the blossoms. An erected growth habit is displayed. The new variety is well suited for providing attractive ornamentation in the landscape.

1 Drawing Sheet

Latin name of genus and species of plant claimed: *Rosa hybrida.*

Variety denomination: 'MEICATESS'.

CROSS REFERENCE TO RELATED APPLCIATIONS

This application claims priority to Plant Breeders' Right Application Number 2021/1798, which was filed at Community Plant Variety Office in the European Union on Jul. 6, 2021, the contents of which are hereby incorporated by reference for all purposes.

BACKGROUND OF THE INVENTION

The new variety of hybrid tea rose plant of the present invention was created by controlled breeding at Le Cannet des Maures, Var, France by artificial pollination wherein two parents were crossed which previously had been studied in the hope that they would contribute the desired characteristics. The female parent (i.e., the seed parent) of the new variety was an unnamed seedling (not patented) from the cross between the 'GOLDEN UNICORN' variety (not patented) and the 'DELGE' variety (not patented). The male parent (i.e., the pollen parent) of the new variety was an unnamed seedling (not patented) from the cross between the 'MEIMALYNA' variety (not patented) and the 'HARLEX' variety (not patented).

The parentage of the new variety can be summarized as follows:

('GOLDEN UNICORN' x 'DELGE') x ('MEIMALYNA' x HARLEX')

The seeds resulting from the above pollination were sown and small plants were obtained which were physically and biologically different from each other. Selective study resulted in the identification of a single plant of the new variety.

The new variety has been found to undergo asexual propagation in Le Cannet des Maures, Var, France by a number of routes, including eye budding, softwood cuttings, hardwood cuttings, and semi-hardwood cuttings. Asexual propagation by the above-mentioned techniques in Le Cannet des Maures, Var, France has shown that the characteristics of the new variety are stable and are strictly transmissible by asexual propagation from one generation to another. Accordingly, the new variety undergoes asexual propagation in a true-to-type manner.

SUMMARY OF THE INVENTION

It was found that the new variety of rose plant of the present invention possesses the following combination of characteristics:

(a) exhibits huge romantic flowers, (b) forms dark pink colored flowers, and (c) emits a strong floral fragrance.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the unnamed seed parent ('GOLDEN UNICORN' x 'DELGE') emits a very weak fragrance, whereas the new variety emits a strong floral fragrance. In addition, the unnamed pollen parent ('MEIMALYNA' x HARLEX') displays red colored flowers, whereas the new variety displays dark pink colored flowers. Moreover, the new variety can be readily distinguished from other similar non-parental varieties. For example, the 'MEIPREHMYR' variety (not patented) displays red colored flowers, whereas the new variety displays dark pink colored flowers.

The new variety has been named 'MEICATESS'.

The first offer for sale of the new variety was May 9, 2021 in France by the inventor or another who obtained the new variety directly or indirectly from the inventor.

BRIEF DESCRIPTION OF THE PHOTOGRAPH

The accompanying photograph of the drawing shows as nearly true as it is reasonably possible to make the same, in a color illustration of this character, typical specimens of the plant parts of the new variety. The rose plants of the new variety were approximately three years of age and were observed during July while budded on their own roots and growing outdoors at Le Cannet des Maures, Var, France. Dimensions in centimeters are indicated at the bottom of the drawing.

Element 1—illustrates a specimen of a young shoot.

Element 2—illustrates a specimen of a floral bud before the opening of the sepals.

Element 3—illustrates a specimen of a floral bud at the opening of the sepals.

Element 4—illustrates a specimen of a floral bud at the opening of the petals.

Element 5—illustrates a specimen of a flower in the course of opening.

Element 6—illustrates a specimen of an open flower—plan view—observe.

Element 7—illustrates a specimen of an open flower—plan view—reverse.

Element 8—illustrates a specimen of a fully open flower—plan view—observe.

Element 9—illustrates a specimen of a fully open flower—plan view—reverse.

Element 10—illustrates a specimen of a floral receptacle showing arrangement of the stamens and pistils.

Element 11—illustrates a specimen of a floral receptacle showing arrangement of the pistils (stamens removed).

Element 12—illustrates a specimen of a flowering stem.

Element 13—illustrates a specimen of a leaf with 3 leaflets—plan view—upper surface.

Element 14—illustrates a specimen of a leaf with 3 leaflets—plan view—under surface.

Element 15—illustrates a specimen of a leaf with 5 leaflets—plan view—upper surface.

Element 16—illustrates a specimen of a leaf with 5 leaflets—plan view—under surface.

Element 17—illustrates a specimen of a leaf with 7 leaflets—plan view—upper surface.

Element 18—illustrates a specimen of a leaf with 7 leaflets—plan view—under surface.

DETAILED BOTANICAL DESCRIPTION

The chart used in the identification of the colors is that of The Royal Horticultural Society (R.H.S. Colour Chart, 2001 edition), London, England. The terminology which precedes reference to the chart has been added to indicate the corresponding color in more common terms. The description is based on the observation of three-years-old specimens of the new variety during July while budded on their own roots and growing outdoors at Le Cannet des Maures, Var, France.

Botanical classification: *Rosa hybrida* cultivar MEICATESS.

Commercial classification: Hybrid Tea Rose Plant.

Plant:

*Habit*.—Erected.

*Height*.—Typically 50 to 80 cm on average.

*Width*.—Typically 30 to 40 cm on average.

Branches:

*Color*.—Young stems: commonly near Green Group 137C strongly covered with near Greyed-Orange Group 165A. Adult wood: commonly near Green Group 137C.

*Length*.—From the crown to the flower is approximately between 50 to 80 cm on average.

*Diameter*.—Approximately between 0.7 to 1.1 cm on average.

*Young shoots*.—Anthocyanin coloration: commonly near Greyed-Purple Group 183A.

*Thorns*.—Configuration on adult stems: upright and elongated on the upper surface and concave on the under surface. Long prickles — quantity: commonly 9 thorns per 15 cm long young stem and commonly 18 thorns per 15 cm long adult stem. Long prickles — base shape: narrow obovate. Long prickles — size: commonly between 0.5 cm to 0.7 cm in length on young stems and commonly between 0.5 cm to 0.9 cm in length on adult stems. Long prickles — color on young stems: commonly near a color between Yellow-Green Group 144B and Yellow-Green Group 144C covered with near Greyed-Orange Group 166B at the pointy half. Long prickles — color on adult stems: commonly near a color between Yellow-Green Group 144B and Yellow-Green Group 144C. Small prickles — quantity: absent.

*Internode*.—Numbers on the entire branch: commonly 10 to 14. Length: commonly between 2.0 cm and 8.0 cm.

Foliage:

*General appearance*.—Dense, dark with a glossy aspect.

*Number of leaflets*.—3, 5, 7; most often 5.

5 *leaflets leaf*.—Length: approximately 15.5 cm on average.

*Terminal leaflet*.—Length: approximately 5.6 cm on average. Width: approximately 4.1 cm on average.

*New foliage*.—Upper surface color: commonly near Green Group 135A covered with anthocyanin coloration of near Greyed-Purple Group 183A. Under surface color: commonly near Green Group 137D coved with anthocyanin coloration of near Greyed-Purple Group 184B.

*Adult foliage*.—Upper surface color: commonly near a color between Green Group 137A and Green Group 135A. Under surface color: commonly near Green Group 137A. Anthocyanin coloration: absent.

Leaflets:

*Shape*.—Tip: cuspidate. Base: obtuse.

*Glossiness of upper surface*.—Strong.

*Texture*.—Thick.

*General appearance*.—Oval.

*Serration*.—Small and single.

*Undulation on the margin*.—Weak.

*Venation*.—Color is commonly near a color between Green Group 143A and Green Group 143B and pattern is imparipinnate.

*Petiole rachis*.—Color of upper surface: commonly near a color between Green Group 143A and Green Group 143B. Color of under surface: commonly near a color between Green Group 143A and Green Group 143B. Texture: upper surface is smooth, under surface is smooth. Rachis of terminal leaflet: length is approximately 5.6 cm on average and diameter is approximately 0.1 cm on average.

*Petioles*.—Upper surface: no glandular. Under surface: no prickles. Color of upper surface: commonly near a color between Green Group 143A and Green Group 143B. Color of under surface: commonly near a color between Green Group 143A and Green Group 143B. Length: approximately 4.2 cm on average. Diameter: approximately 0.1 cm on average.

*Stipules*.—Length: approximately 2.0 cm on average. Width: approximately 0.6 cm on average. Color of upper surface: commonly near a color between Green Group 143A Green Group 143B. Color of under surface: commonly near a color between Green Group 143A and Green Group 143B.

Inflorescence:

*Number of flowers per stem*.—Typically 1 flower per stem.

*Lastingness of the bloom*.—On the plant: approximately 10 days on average. In vase: approximately 15 days on average.

*Bud*.—Shape: globular. Size: medium. Length: approximately 2.0 cm on average. Width: approximately 2.5 cm on average. Color as calyx breaks: upper surface: commonly near Red Group 52A, basal spot is very little and near Yellow Group 3B. under surface: commonly near Red Group 53C, basal spot is very little and near Yellow Group 3C.

*Sepals*.—Number: commonly 5. Length: approximately 3.0 cm on average. Width: approximately 1.1 cm on average. Shape: at the top: slightly elongated and narrow, at the base: abroad. Extensions: absent or very weak extensions. Upper surface: texture: tomentous. color: commonly near Yellow-Green Group 144B with Green Group 137B on the edges, covered with silky fur near White Group 155D. Under surface: texture: smooth. color: commonly near Yellow-Green Group 144A with Green Group 137A on the edges.

*Receptacle*.—Color: commonly near Yellow-Green Group 144A. Length: approximately 0.4 cm on average. Width: approximately 0.9 cm on average. Surface: smooth. Shape: funnel shaped.

*Peduncle*.—Length: approximately 8.3 cm on average. Width: approximately 0.4 cm on average. Surface: smooth. Color: commonly near Yellow-Green Group 144A.

*Flower*.—Average size when open: approximately 14.0 cm. Shape: flat cup shaped. Shape when viewed from above: round. Shape of the upper part of the flower profile: flat. Shape of the lower part of the flower profile: flat. Type: very double. Number of petals under normal conditions: typically between 150 to 250 petals. Petals: shape: rounded. texture: soft. length: commonly between 3.2 cm to 5.4 cm. width: commonly between 2.3 cm to 4.4 cm. Undulation of the petal: very weak. Reflexing of the petal: absent. Petal incision: absent. Petal arrangement: imbricated with some petaloids (look like deformed half petals). Petal drop: petals drop off cleanly before drying. Fragrance: strong floral fragrance. Color when opening: basal spot on the upper surface: very small, commonly near Yellow Group 3C. upper surface: commonly near a color between Red-Purple Group 58C and near Red-Purple Group 58D. basal spot on the under surface: very small, commonly near Yellow Group 3D. under surface: commonly near a color between Red-Purple Group 57C and Red-Purple Group 57D. Color of the open flower: basal spot on the upper surface: small, commonly near Yellow-White Group 158C. upper surface of the flower: commonly near Red-Purple Group 64D. basal spot on the under surface: small, commonly near Yellow-White Group 158C. under surface of the flower: commonly near Red-Purple Group 64C. Anthers: number is 10 on average, length is approximately 0.3 cm on average, width is approximately 0.1 cm on average, coloration is commonly near Yellow Group 13B and the under surface is near Yellow Group 13C with a little touch of near Red-Purple Group 58B, and arrangement is regular around styles. Filaments: length is approximately 0.4 cm on average and coloration is commonly near Yellow Group 5A. Styles: length is approximately 0.7 cm on average, coloration is commonly near White Group 155B at the base with the upper half near Red-Purple Group 58B, and number is approximately 110 on average. Stigmas: size is approximately 0.1 cm on average and coloration is commonly near Greyed-Yellow Group 161C. Pollen: not available at this stage. Hips: not available at this stage.

Development:

*Vegetation*.—Glossy and strong.

*Blooming*.—Early in the season, typically from May to October in France and intermittent.

*USDA hardiness zone*.—Zone 5.

*Tolerance to disease*.—Good, and particularly against Powdery Mildew (Podosphaera pannosa).

The new 'MEICATESS' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of rose plant named 'MEI-CATESS' characterized by the following combination of characteristics:

(a) exhibits huge romantic flowers,
(b) forms dark pink colored flowers, and
(c) emits a strong floral fragrance;
substantially as herein shown and described.

* * * * *

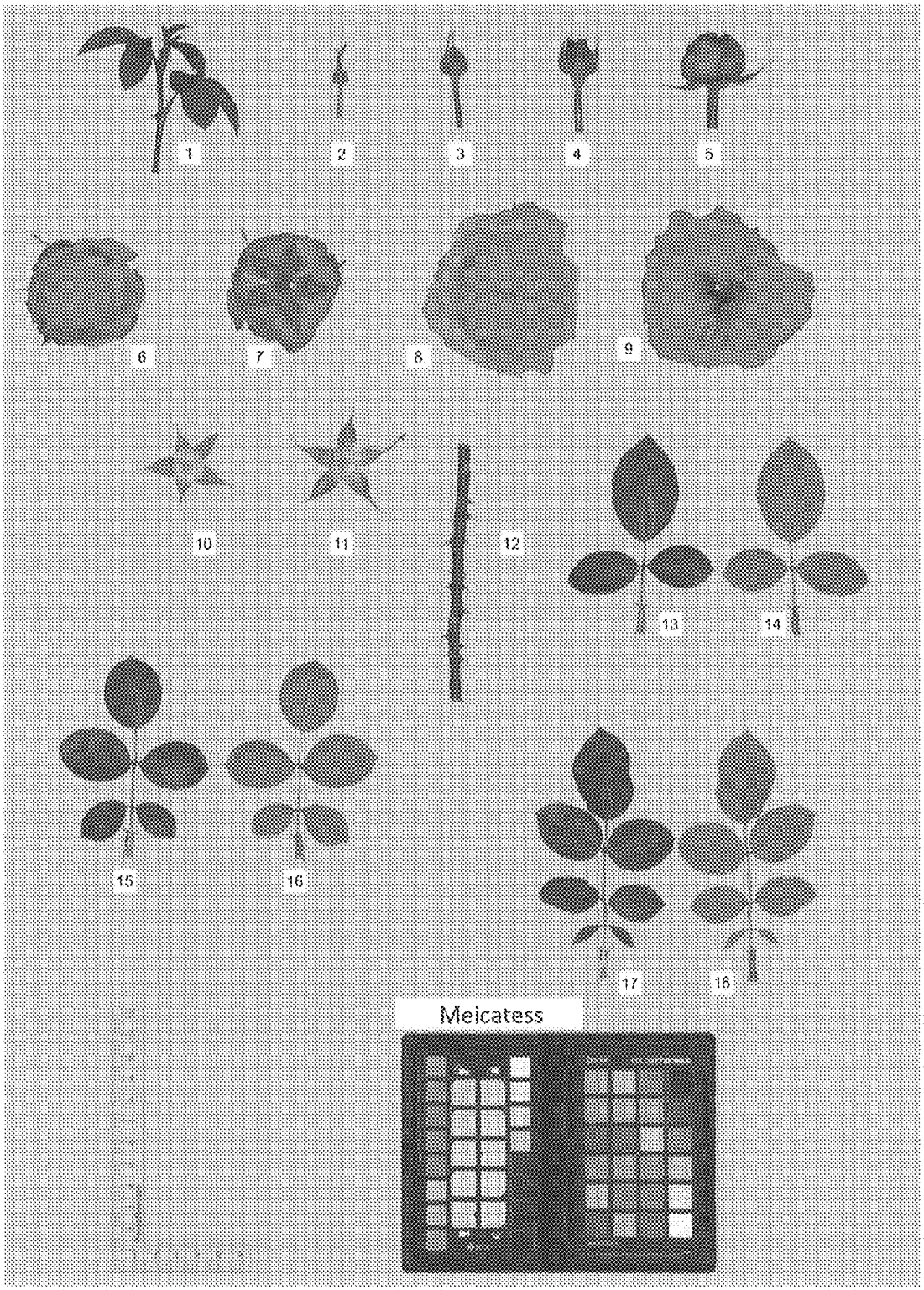
1
2
3
4
5
6
7
8
9
10
11
12
13
14
15
16
17
18
Meicatess